May 12, 1964 E. S. BOERNER Plant Pat. 2,402
ROSE PLANT
Filed June 18, 1963
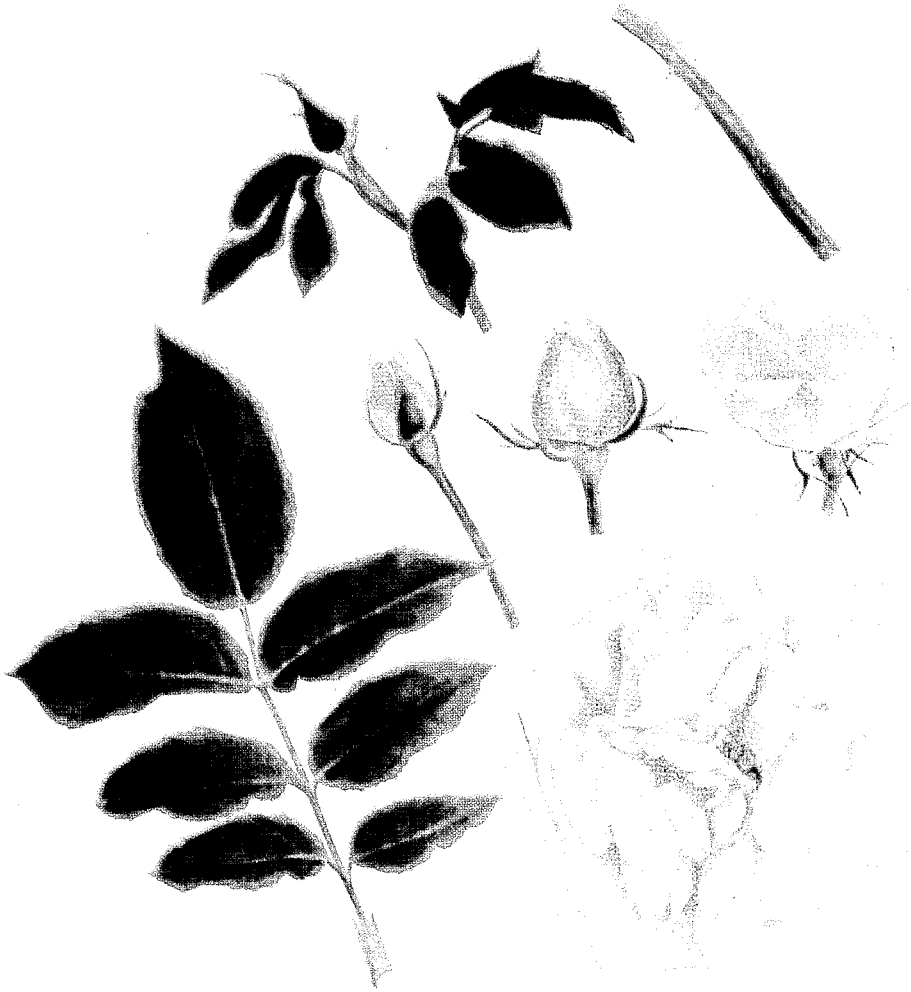
Inventor.
E. S. Boerner
By: Robert Cobb
Attorneys.

United States Patent Office

Plant Pat. 2,402
Patented May 12, 1964

2,402
ROSE PLANT

Eugene S. Boerner, Newark, N.Y., assignor to Jackson & Perkins Company, Newark, N.Y., a corporation of New York Filed June 18, 1963, Ser. No. 288,847
1 Claim. (Cl. Plt.—17)

The present invention relates to a new and distinct variety of rose plant of the hybrid tea class, which was originated by me by crossing an unnamed and unpatented seedling of "Pageant" (Plant Patent No. 1,252) with an unnamed and unpatented seedling of "Diamond Jubilee" (Plant Patent No. 824).

The primary objective of this breeding was to produce a new rose variety having the good keeping flower qualities of "Diamond Jubilee," combined with the good plant and foliage qualities of the latter, but the flowers of which are of a different color from those of the parent varieties. This objective was fully achieved, along with other desirable improvements, as evidenced by the following unique combination of characteristics which are outstanding in the new variety and which distinguish it from its parents, as well as from all other varieties of which I am aware:

(1) A vigorous habit of growth;
(2) Abundant and healthy Varley's Green foliage;
(3) A distinctive and attractive general color tonality of the flowers corresponding to Geranium Pink, lightly overcast with Scarlet; and
(4) A strong rose geranium flower fragrance.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—An unnamed seedling of "Pageant."
*Pollen parent.*—An unnamed seedling of "Diamond Jubilee."

Classification:
*Botanic.*—Hybrid tea.
*Commercial.*—Hybrid tea.

*Flower*

(Observations made from specimens grown outdoors at Newark, New York, near mid-morning during the middle part of the month of September.)

Blooming habit: Recurrent—continuous.

Bud:
*Size.*—Large.
*Form.*—Ovoid; is not affected by wet or hot weather.
*Color.*—When sepals first divide—Nopal Red, Plate 1. When petals begin to unfurl—Jasper Red, Plate 13, with edges lightly overcast with Nopal Red, Plate 1. When half-blown: inside of petals—Rose Doree, Plate 1, very lightly overcast with Scarlet Red, Plate 1; reverse of petals—Jasper Red, Plate 13, lightly overcast with Scarlet, Plate 1.
*Sepals.*—Branched; curl back when petals begin to unfurl. Color: inside—Corydalis Green, Plate 41; outside—Cress Green, Plate 31, very lightly overcast with Oxblood Red, Plate 1.

*Calyx.*—Color—Light Bice Green, Plate 17. Shape—funnel. Size—small. Aspect—smooth. Odor when rubbed—none.
*Peduncle.*—Length — medium. Aspect — Rough. Strength—erect; slender. Color—Light Bice Green, Plate 17, lightly overcast with Carmine, Plate 1.
*Opening.*—Opens up well; is not affected by adverse weather conditions.

Bloom:
*Size.*—Large. Average size when fully expanded—from 5 inches to 5½ inches.
*Borne.*—Both singly and several together.
*Stems.*—Medium length; strong.
*Form (when first open).*—High-centered. Permanence—retains its form to the end.
*Petalage.*—Double (full but open center). Number of petals under normal conditions—from 35 to 40.
*Color.*—Center of flower—Rose Doree, Plate 1, very lightly overcast with Scarlet, Plate 1. Outer petals—Rose Doree, Plate 1, very lightly overcast with Geranium Pink, Plate 1. Base of petals (aiglet)—Lemon Chrome, Plate 4. Inside of petals—Germanium Pink, Plate 1, lightly overcast with Scarlet, Plate 1. Reverse of petals—Eosine Pink, Plate 1. Generally tonality from a distance—Geranium Pink, Plate 1, lightly overcast with Scarlet, Plate 1.
*Discoloration.*—General tonality at end of first day—Rose Doree, Plate 1, lightly overcast with Scarlet, Plate 1. Second day—Geranium Pink, Plate 1, lightly overcast with Scarlet, Plate 1. Third day—Rose Doree, Plate 1, lightly overcast with Geranium Pink, Plate 1.

Petals:
*Texture.*—Thick; is not affected by wet or hot weather.
*Appearance.*—Inside—satiny. Outside—shiny.
*Form.*—Round.
*Arrangement.*—Imbricated (regularly arranged shingle-like).
*Petaloids in center.*—Few; small.
*Persistence.*—Drop off cleanly.
*Fragrance.*—Strong. Nature—rose geranium.
*Lasting quality.*—On the plant—long. As cut flower—long.

*Genital Organs*

Stamens, Anthers: Large size; many; regularly arranged around styles. Color—Apricot Yellow, Plate 4.
Stamens, filaments (threads): Long. Color—Scarlet Red, Plate 1.
Pollen: Color—Maize Yellow, Plate 4.
Styles: Bunched; uneven length; short; thin.
Stigmas: Color—Pinkish Buff, Plate 29.
Ovaries: Some protruding from calyx.
Hips: None.
Seeds: None.

*Plant*

Form: Bush.
Growth: Vigorous; upright.
Foliage: Compound of 5–7 leaflets.
*Size.*—Medium.
*Quantity.*—Abundant and healthy.
*Color.*—New foliage: upper side—Oxblood Red, Plate 1; under side—Chromium Green, Plate 32, overcast with Brazil Red, Plate 1. Old foliage: upper side—Varley's Green, Plate 18; under side—Light Cress Green, Plate 31.
*Shape.*—Oval pointed.

*Texture.*—Upper side—leathery. under side—smooth.

*Ribs and veins.*—Ordinary.

*Edge.*—Serrated (saw-toothed).

*Serration.*—Both double and single; small.

*Leaf stem.*—Color— Turtle Green, Plate 32. Under side—prickly.

*Stipules.*—Medium length; slightly bearded.

Wood:

*New wood.*—Color—Yellowish Oil Green, Plate 5. Bark—smooth.

*Old wood.*—Color—Forest Green, Plate 17. Bark—smooth.

Thorns:

*Thorns.*—Quantity: on main stalks from base—ordinary; on laterals from stalk—ordinary. Form—narrow base; medium length; some straight and some hooked downward. Color (when young)—Eugenia Red, Plate 13. Position—irregular.

*Prickles.*—Quantity: on main stalks—none; on laterals—none.

*Short needles.*—Quantity: on main stalks—none; on laterals—none.

I claim:

A new and distinct variety of Rose plant of the hybrid tea class, substantially as herein shown and described, characterized particularly as to novelty by the unique combination of a vigorous habit of growth, abundant and healthy Varley's Green foliage, a distinctive and attractive general color tonality of the flowers corresponding to Geranium Pink, lightly overcast with Scarlet, and a strong rose geranium flower fragrance.

No references cited.